(12) United States Patent
Ishikawa et al.

(10) Patent No.: US 9,027,745 B2
(45) Date of Patent: May 12, 2015

(54) SORTING SYSTEM AND SORTING METHOD FOR ABSORBENT PRODUCTS

(75) Inventors: Osamu Ishikawa, Kanonji (JP); Miwa Iida, Kanonji (JP)

(73) Assignee: Unicharm Corporation, Ehime (JP)

( * ) Notice: Subject to any disclaimer, the term of this patent is extended or adjusted under 35 U.S.C. 154(b) by 19 days.

(21) Appl. No.: 13/824,579

(22) PCT Filed: Sep. 28, 2011

(86) PCT No.: PCT/JP2011/072904
§ 371 (c)(1),
(2), (4) Date: Mar. 18, 2013

(87) PCT Pub. No.: WO2012/043865
PCT Pub. Date: Apr. 5, 2012

(65) Prior Publication Data
US 2013/0180835 A1 Jul. 18, 2013

(30) Foreign Application Priority Data

Sep. 30, 2010 (JP) .................................. 2010-223041

(51) Int. Cl.
*B65G 47/82* (2006.01)
*B65G 47/52* (2006.01)
*B65H 29/60* (2006.01)
(Continued)

(52) U.S. Cl.
CPC .......... *B65G 47/52* (2013.01); *A61F 13/15764* (2013.01); *B65G 47/82* (2013.01); *B65H 29/58* (2013.01); *B65H 2404/1112* (2013.01); *B65H 2404/633* (2013.01); *B65H 2404/67* (2013.01); *B65H 2701/1924* (2013.01)

(58) Field of Classification Search
None
See application file for complete search history.

(56) References Cited

U.S. PATENT DOCUMENTS

| 5,234,211 A | 8/1993 | Olexy |
| 5,879,505 A | 3/1999 | Fujisawa et al. |

(Continued)

FOREIGN PATENT DOCUMENTS

| JP | 1-252457 A | 10/1989 |
| JP | 5-178452 A | 7/1993 |
| JP | 10-010750 A | 1/1998 |
| JP | 2002-079187 A | 3/2002 |
| JP | 2009-227460 A | 10/2009 |

OTHER PUBLICATIONS

International Search Report corresponding to PCT/JP2011/072904, filed Nov. 8, 2011.

(Continued)

*Primary Examiner* — Kavel Singh
(74) *Attorney, Agent, or Firm* — Lowe Hauptman & Ham, LLP

(57) ABSTRACT

This distributing device for absorbent articles is provided with a main conveyor path, a branch conveyor path that branches from the main conveyor path, a main conveyor path that conveys absorbent articles along the main conveyor path, a diverting mechanism that diverts absorbent articles in the main conveyor path from the main conveyor path to the branch conveyor path, and a branch conveyor mechanism that conveys the absorbent articles diverted by the diverting mechanism along the branch conveyor path. The diverting mechanism is provided with a diverting part for diverting the absorbent articles. The diverting part moves without stopping, entering the main conveyor path from a standby position outside the main conveyor path and then, after leaving the main conveyor path, returning to the standby position.

7 Claims, 5 Drawing Sheets

(51) Int. Cl.
*A61F 13/15* (2006.01)
*B65H 29/58* (2006.01)

(56) References Cited

U.S. PATENT DOCUMENTS 7,617,656 B2 * 11/2009 Wiedmann .................. 53/429
2008/0223537 A1 9/2008 Wiedmann

OTHER PUBLICATIONS

Extended European Search Report issued Mar. 12, 2014, corresponds to European patent application No. 11829417.2.
Office Action dated Jun. 6, 2014, corresponds to Philippine patent application No. 1/2013/500582.

* cited by examiner

SORTING SYSTEM AND SORTING METHOD FOR ABSORBENT PRODUCTS

RELATED APPLICATIONS

The present application is a National Phase of International Application Number PCT/JP2011/072904, filed Sep. 28, 2011, and claims priority from Japanese Application Number 2010-223041, filed Sep. 30, 2010.

TECHNICAL FIELD

The present invention relates to a sorting system and sorting method for absorbent products.

BACKGROUND ART

Known in the art is a sorting system for products which is provided with a main conveyor path, a branch conveyor path which is branched from the main conveyor path, a main conveyor mechanism which conveys a product along the main conveyor path, a sorting mechanism which diverts a product in the main conveyor path from the main conveyor path to the branch conveyor path, and a branch conveyor mechanism which conveys the product which was diverted by the sorting mechanism along the branch conveyor path, in which sorting system the sorting mechanism is provided with a sorting member which diverts an absorbent product, and the sorting member descends from a standby position outside the main conveyor path to the inside of the main conveyor path, then rises and retracts from the main conveyor path and returns to the standby position (see PLT 1).

CITATION LIST

Patent Literature

PLT 1 Japanese Patent Publication (A) No. 2002-79187

SUMMARY OF INVENTION

Technical Problem

In the above-mentioned sorting system, the sorting member is temporarily stopped inside the main conveyor path. Therefore, the time when the sorting member is positioned inside the main conveyor path becomes relatively long.

However, if the time when the sorting member is positioned in the main conveyor path is long, the succeeding product which should be conveyed along the main conveyor path is also likely to be diverted by the sorting member to the branch conveyor path. That is, the products are likely to be unable to be accurately sorted. This problem is particularly serious when conveying products along the main conveyor path at a high speed.

Solution to Problem

According to one aspect of the present invention, there is provided a sorting system for an absorbent product which is provided with: a main conveyor path; a branch conveyor path which is branched from the main conveyor path; a main conveyor mechanism which conveys an absorbent product along the main conveyor path; a sorting mechanism which diverts an absorbent product in the main conveyor path from the main conveyor path to the branch conveyor path; and a branch conveyor mechanism which conveys an absorbent product which was diverted by the sorting mechanism along the branch conveyor path, wherein the sorting mechanism is provided with a sorting member which diverts the absorbent product, and wherein the sorting member is moved, without being stopped, from a standby position outside the main conveyor path to the inside of the main conveyor path, then is retracted from the main conveyor path and is returned to the standby position.

Further, according to another aspect of the present invention, there is provided a sorting method for absorbent products including: conveying an absorbent product along a main conveyor path, using a main conveyor mechanism; diverting the absorbent product in the main conveyor path to a branch conveyor path which is branched from the main conveyor path, using a sorting mechanism; and conveying the absorbent product which was diverted by the sorting mechanism along the branch conveyor path, using a branch conveyor mechanism, wherein the sorting mechanism is provided with a sorting member which diverts an absorbent product, and wherein the sorting member is moved, without being stopped, from a standby position outside the main conveyor path to the inside of the main conveyor path, then is retracted from the main conveyor path and returned to the standby position.

Advantageous Effects of Invention

It is possible to make a sorting member quickly retract from a main conveyor path, so absorbent products can be accurately sorted.

DESCRIPTION OF EMBODIMENTS

Figure 1:
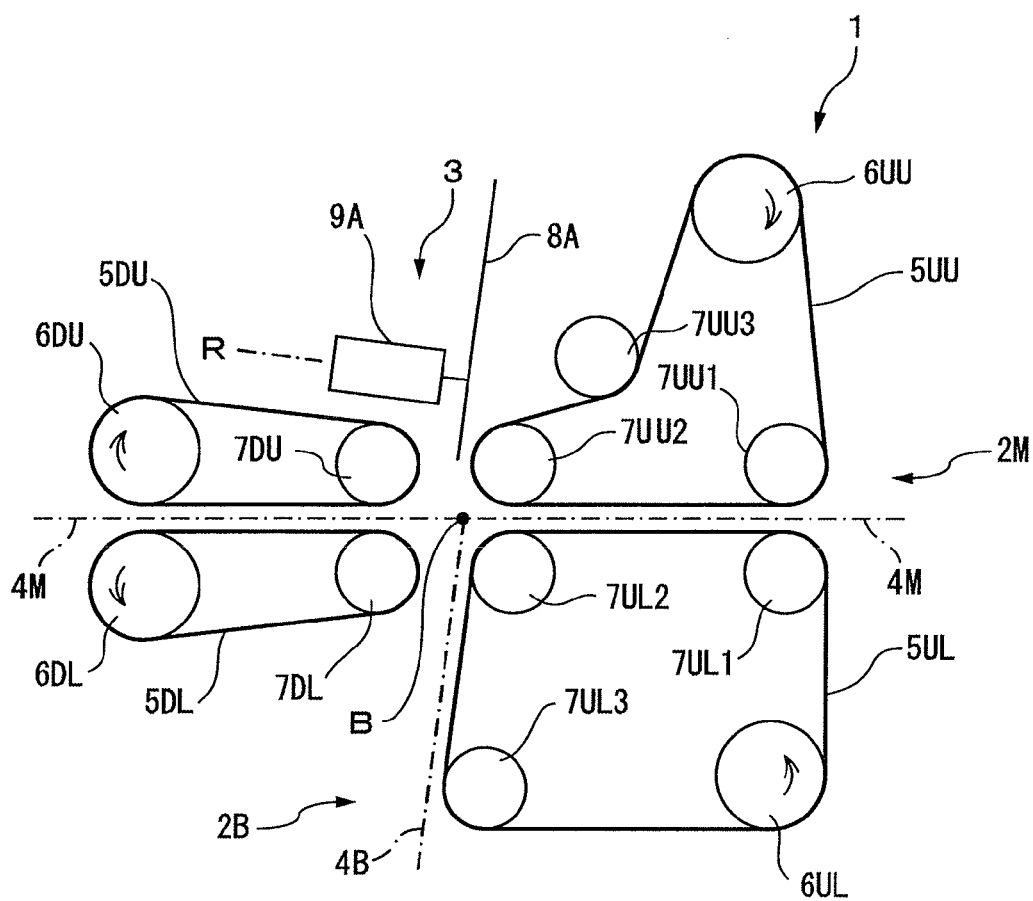
FIG. 1 is a side view of a sorting system.

FIG. 1 shows a sorting system 1 for absorbent products such as sanitary napkins, panty liners, incontinence pads, and diapers.

Referring to FIG. 1, the sorting system 1 is provided with a main conveyor path 4M and a branch conveyor path 4B which has been branched from the main conveyor path 4M at a branching point B. In the example shown in FIG. 1, the main conveyor path 4M extends in the horizontal direction in a straight line, while the branch conveyor path 4B extends at a slant from the main conveyor path 4M downward in a straight line.

The sorting system 1 is further provided with a main conveyor mechanism 2M which conveys the absorbent products along the main conveyor path 4M, a sorting mechanism 3 which diverts absorbent products in the main conveyor path 4M from the main conveyor path 4M to the branch conveyor path 4B, and a branch conveyor mechanism 2B which conveys absorbent products which were diverted by the sorting mechanism 3 along the branch conveyor path 4B.

The main conveyor mechanism 2M is provided with a pair of conveyor belts 5UU and 5UL which are arranged facing each other at an upstream side of the sorting mechanism 3 and a pair of conveyor belts 5DU and 5DL which are arranged facing each other at a downstream side of the sorting mechanism 3.

The conveyor belt 5UU is strung around a drive pulley 6UU and idle pulleys 7UU1, 7UU2, and 7UU3 and is rotated by the drive pulley 6UU. Similarly, the conveyor belt 5UL is strung around a drive pulley 6UL and idle pulleys 7UL1, 7UL2, and 7UL3 and is rotated by the drive pulley 6UL. Further, the conveyor belt 5DU is strung around the drive pulley 6DU and idle pulley 7DU and is rotated by the drive pulley 6DU. Similarly, the conveyor belt 5DL is strung around the drive pulley 6DL and idle pulley 7DL and is rotated by the drive pulley 6DU.

The part of the conveyor belt 5UU between the pulleys 7UU1 and 7UU2 and the part of the conveyor belt 5UL between the pulleys 7UL1 and 7UL2 extend substantially parallel to the main conveyor path 4M, while the lower side part of the conveyor belt 5DU between the pulleys 6DU and 7DU and the upper side part of the conveyor belt 5DL between the pulleys 6DL and 7DL also extend substantially parallel to the main conveyor path 4M.

The absorbent products are conveyed while being gripped between the part of the conveyor belt 5UU between the idle pulleys 7UU1 and 7UU2 and the conveyor belt 5UL between the idle pulleys 7UL1 and 7UL2, then are conveyed while being gripped between the conveyor belt 5DU and the conveyor belt 5DL, therefore are conveyed along the main conveyor path 4M. In this case, the conveyor belts 5UU, 5UL, 5DU, and 5DL are moved at substantially equal speeds with each other.

On the other hand, the branch conveyor mechanism 2B is provided with the conveyor belt 5UL which is common to the main conveyor mechanism 2M. The part of the conveyor belt 5UL between 7UL2 and 7UL3 extends substantially parallel to the branch conveyor path 4M. Absorbent products which are diverted by the sorting mechanism 3 to the branch conveyor path 4M are conveyed by the conveyor belt 5UL between the idle pulleys 7UL2 and 7UL3, therefore are conveyed along the branch conveyor path 4B. In this way, in the example shown in FIG. 1, the conveyance speed along the main conveyor path 4M and the conveyance speed along the branch conveyor path 4B are made equal to each other. Note that the branch conveyor mechanism 2B may also be provided with a separate conveyor belt from the main conveyor mechanism 2M. Further, the conveyor belts 5UU, 5UL, 5DU, and 5DL may also be configured from belts of types which hold the conveyed absorbent products by negative pressure.

Figure 2:
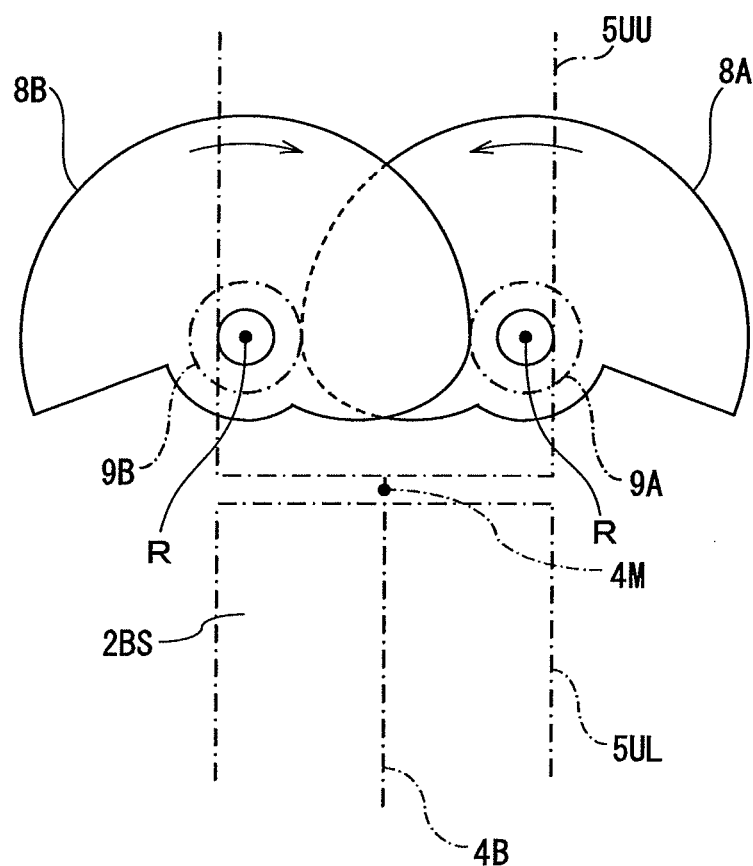
FIG. 2 is a view showing sorting members.

Referring to FIG. 1 and also FIG. 2, the sorting mechanism 3 is provided with, for example, a pair of sorting members 8A and 8B for sorting the absorbent products and rotation devices 9A and 9B such as electric motors for making the corresponding sorting members 8A and 8B rotate about axes of rotation R. These sorting members 8A and 8B are plate shaped and are arranged in a direction cutting across the main conveyor path 4M and branch conveyor path 4B, in particular in a perpendicular direction.

In this case, the axes of rotation R are substantially parallel to the main conveyor path 4M and are substantially vertical to the branch conveyor path 4B, therefore the sorting members 8A and 8B are rotated substantially parallel to the conveyor surface 2BS of the branch conveyor mechanism 2B (FIG. 2). Further, the sorting members 8A and 8B are made to move by substantially the same speed as the conveyance speed of the branch conveyor mechanism 2B, that is, the movement speed of the conveyor belt 5UL, in other words, within a range of ±10% of the conveyor belt movement speed. Furthermore, the sorting members 8A and 8B are arranged with respect to the conveyor belt 5UL so that the absorbent products are gripped between the rotating sorting members 8A and 8B and conveyor belt 5UL. In other words, the distance between the sorting members 8A and 8B and the conveyor belt 5UL is set so that the absorbent products are gripped between the rotating sorting members 8A and 8B and conveyor belt 5UL.

In FIG. 1 and FIG. 2, the sorting members 8A and 8B are at the standby position outside the main conveyor path 4M. In this case, the sorting members 8A and 8B partially overlap.

When absorbent products A should be conveyed along the main conveyor path 4M, the sorting members 8A and 8B are held at the above-mentioned standby position. As a result, the absorbent products A are conveyed by the conveyor belts 5UU and 5UL, then are conveyed by the conveyor belts 5DU and 5DL.

When the absorbent products A should be conveyed along the branch conveyor path 4B, the sorting members 8A and 8B are rotated synchronously with each other. As a result, the sorting members 8A and 8B leave the standby position and enter into the main conveyor path 4M whereby the absorbent products A are diverted from the main conveyor path 4M to the branch conveyor path 4B.

Figure 3:
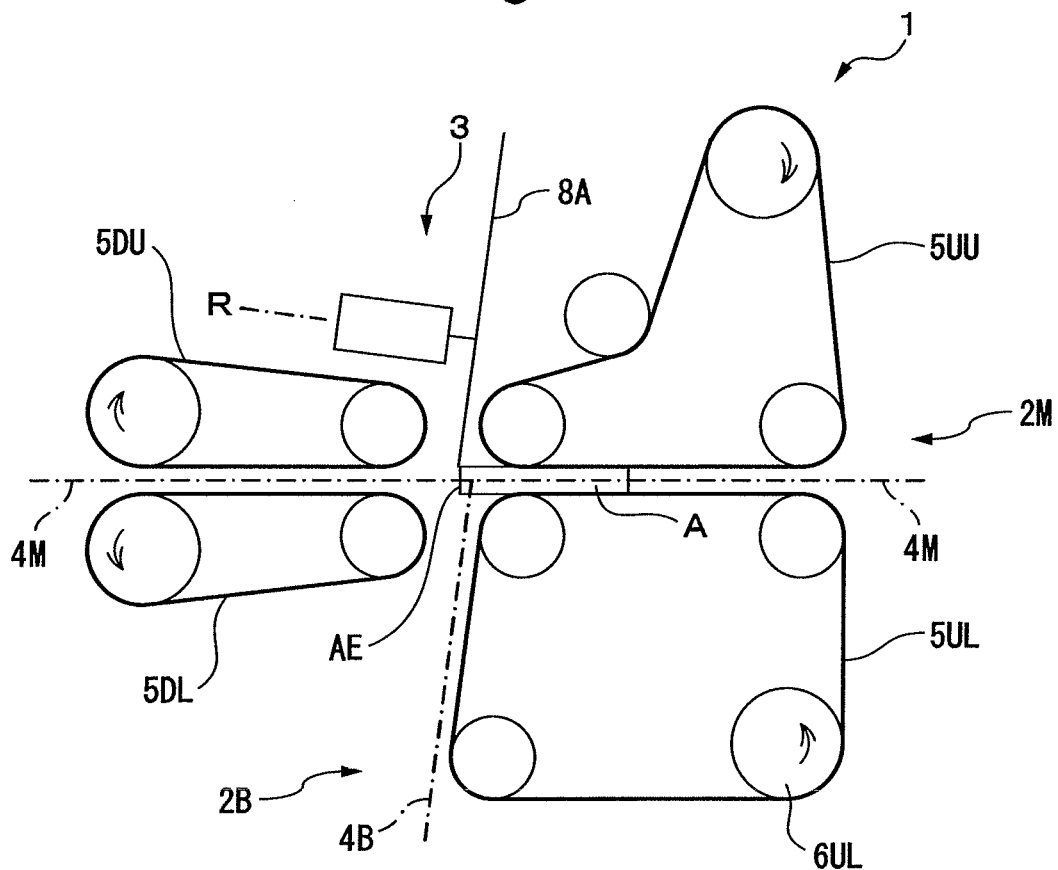
FIG. 3 is a view showing a sorting system for explaining a sorting action.
Figure 4:
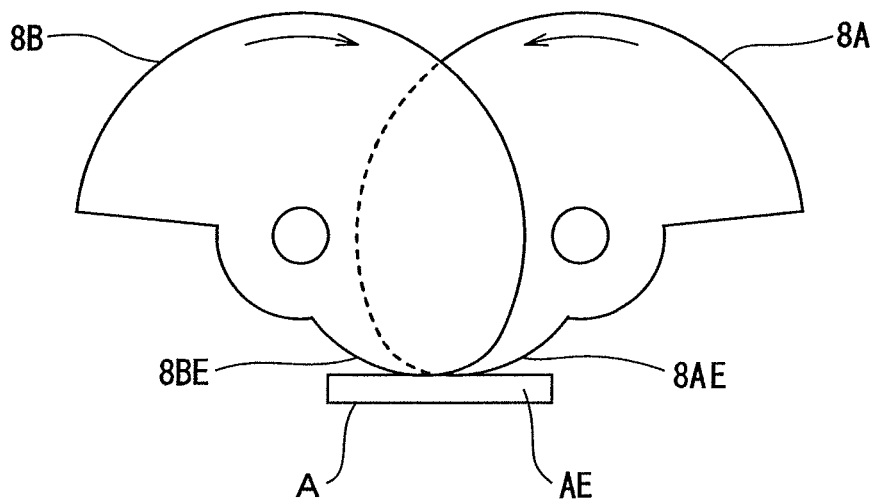
FIG. 4 is a view showing a sorting system for explaining a sorting action.

In this case, the rotation operation of the sorting members 8A and 8B is started so that the sorting members 8A and 8B are positioned inside the main conveyor path 4M before the absorbent products A which should be diverted to the branch conveyor path 4B reach the branching point B. In this embodiment of the present invention, as shown in FIG. 3 and FIG. 4, the rotation operation of the sorting members 8A and 8B is started so that the front ends AE of the absorbent products A strike the leading end parts 8AE and 8BE of the sorting members 8A and 8B.

Figure 5:
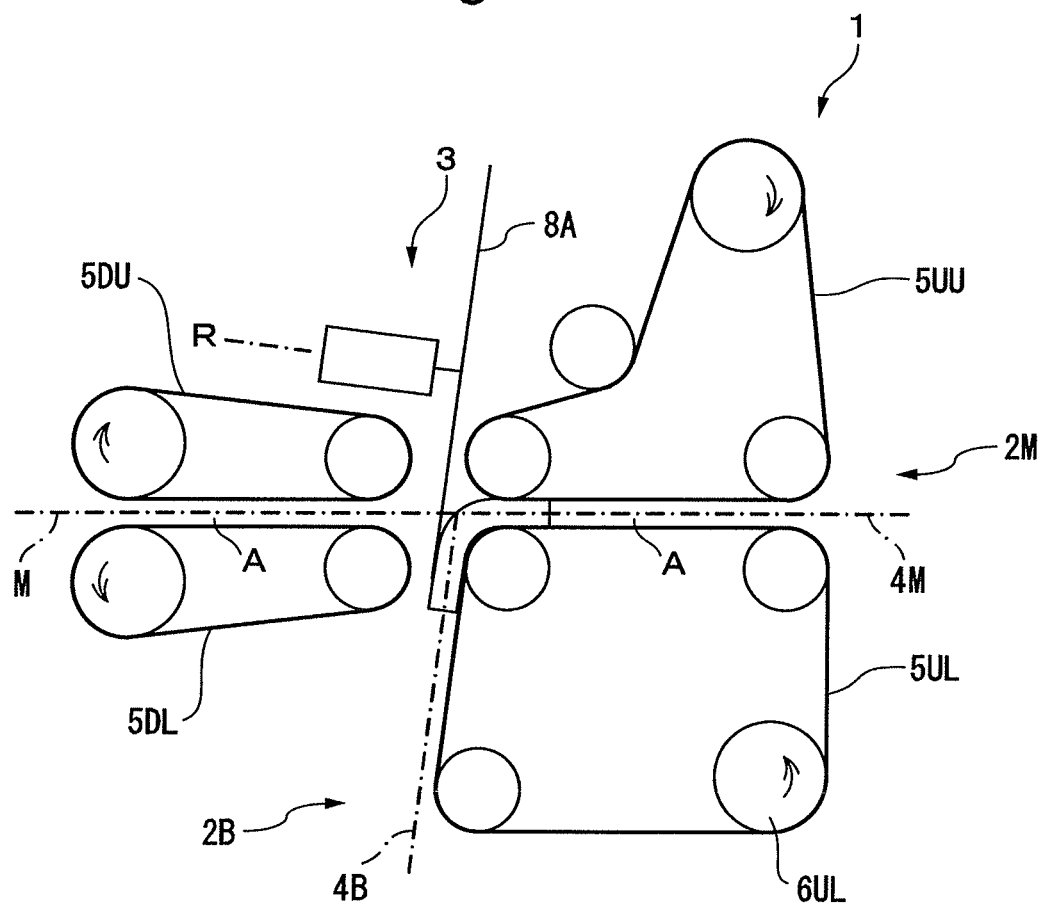
FIG. 5 is a view showing a sorting system for explaining a sorting action.
Figure 6:
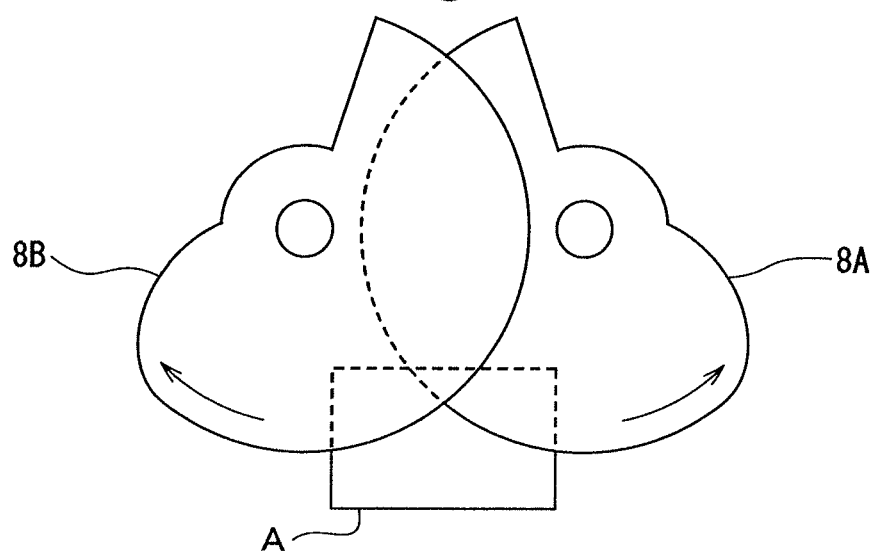
FIG. 6 is a view showing a sorting system for explaining a sorting action.

Next, as shown in FIG. 5 and FIG. 6, the absorbent products A are gripped between the rotating sorting members 8A and 8B and the conveyor belt 5UL while being conveyed along the branch conveyor path 4B. In this way, the absorbent products A are diverted or the conveyance direction of the absorbent products A is changed.

Figure 7:
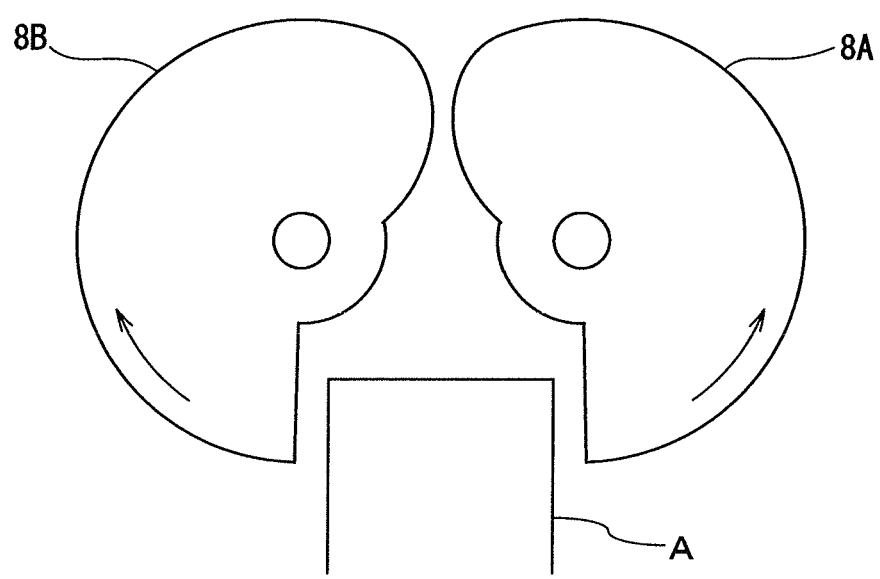
FIG. 7 is a view showing a sorting system for explaining a sorting action.

The sorting members 8A and 8B are further rotated and, as shown in FIG. 7, are retracted from the main conveyor path 4M to separate from the absorbent products A. Next, the sorting members 8A and 8B are further rotated and returned to the standby position (FIG. 1 and FIG. 2). When the sorting members 8A and 8B return to the standby position, rotation stops and, therefore, the sorting members 8A and 8B are held at the standby position.

In this case, the sorting members 8A and 8B are moved without stopping so as to leave the standby position, cut across the main conveyor path 4M, and return to the standby position.

On this point, it can be considered that the sorting members 8A and 8B are rotated in a single direction so as to leave the standby position, cut across the main conveyor path 4M, and return to the standby position. That is, the sorting members 8A and 8B which cut across the main conveyor path 4M are returned to the standby position without again cutting across the main conveyor path 4M. Alternatively, it can also be considered that the sorting members 8A and 8B are retracted from the main conveyor paths 8A and 8B along a path different from the path followed when entering the main conveyor paths 8A and 8B.

Whatever the case, in this embodiment of the present invention, the sorting members 8A and 8B can be made to quickly retract from the main conveyor path 4M. Therefore, subsequent absorbent products which should be conveyed along the main conveyor path 4M can be prevented from being diverted by the sorting members 8A and 8B to the branch conveyor path 4B. Therefore, even when the absorbent products are conveyed at a high speed, the absorbent products can be accurately sorted.

Further, as explained above, the sorting members 8A and 8B are rotated substantially in parallel with the conveyor surface 2BS of the branch conveyor mechanism 2B at substantially equal speeds with the movement speed of the conveyor belt 5UL. Further, the sorting members 8A and 8B are arranged with respect to the conveyor belt 5UL so that the absorbent products are gripped between the sorting members 8A and 8B and the conveyor belt 5UL. As a result, the absorbent products A can be reliably diverted to the branch conveyor path 4B.

In the above embodiment, a pair of sorting members 8A and 8B which are moved synchronously with each other are provided. However, there may also be a single sorting member or three or more members.

Further, it is also possible to make a plurality of sorting members move independently from each other. That is, for example, when diverting a preceding absorbent product to the branch conveyor path 4B, it is also possible to make only the sorting member 8A rotate, while when diverting a succeeding absorbent product to the branch conveyor path 4B, it is possible to make only the sorting member 8B rotate.

REFERENCE SIGNS LIST 1 sorting system
2M main conveyor mechanism
2B branch conveyor mechanism
3 sorting mechanism
4M main conveyor path
4B branch conveyor path
8A, 8B sorting members
A absorbent products

The invention claimed is:

1. A sorting system for an absorbent product, said sorting system comprising:
   a main conveyor path;
   a branch conveyor path which is branched from the main conveyor path;
   a main conveyor mechanism configured to convey an absorbent product along the main conveyor path;
   a sorting mechanism configured to divert an absorbent product in the main conveyor path from the main conveyor path to the branch conveyor path; and
   a branch conveyor mechanism configured to convey an absorbent product which was diverted by the sorting mechanism along the branch conveyor path,
   wherein the sorting mechanism includes a sorting member which is configured to divert the absorbent product, and
   wherein the sorting member is configured to selectively divert the absorbent product from the main conveyor path to the branch conveyor path by moving, without stopping, from a standby position outside the main conveyor path to the inside of the main conveyor path, and then without stopping inside the main conveyor path, retracting from the main conveyor path and returning to the standby position.

2. A sorting system as set forth in claim 1, wherein the sorting member is configured to be rotated in one direction so as to leave the standby position, cut across the main conveyor path, and return to the standby position.

3. A sorting system as set forth in claim 2, wherein the sorting member is configured to move substantially parallel to a conveyor surface of the branch conveyor mechanism.

4. A sorting system as set forth in claim 3, wherein the sorting members is configured to move by substantially an equal speed with a conveyance speed of the branch conveyor mechanism.

5. A sorting system as set forth in claim 4, wherein the sorting member is arranged with respect to the branch conveyor mechanism so that an absorbent product is gripped between the moving sorting member and the branch conveyor mechanism.

6. A sorting system as set forth in claim 1, wherein the sorting mechanism is provided with a pair of sorting members which are arranged in a direction cutting across the main conveyor path and branch conveyor path.

7. A sorting method for absorbent products, said method including:
   conveying an absorbent product along a main conveyor path, using a main conveyor mechanism;
   selectively diverting the absorbent product in the main conveyor path to a branch conveyor path which is branched from the main conveyor path, using a sorting mechanism; and
   conveying the absorbent product which was selectively diverted by the sorting mechanism along the branch conveyor path, using a branch conveyor mechanism,
   wherein the sorting mechanism is provided with a sorting member which selectively diverts the absorbent product, and
   wherein the sorting member selectively diverts the absorbent product from the main conveyor path to the branch conveyor path by moving, without stopping, from a standby position outside the main conveyor path to the inside of the main conveyor path, and then without stopping inside the main conveyor path, retracting from the main conveyor path and returning to the standby position.

* * * * *